United States Patent [19]
Gloth et al.

[11] Patent Number: 5,749,870
[45] Date of Patent: May 12, 1998

[54] ELECTRODE FOR COAGULATION AND RESECTION

[75] Inventors: David Gloth, Boston; Jeffrey A. Dann, Worcester, both of Mass.

[73] Assignee: NEBL, Inc., Worcester, Mass.

[21] Appl. No.: 701,916

[22] Filed: Aug. 23, 1996

[51] Int. Cl.⁶ .................................................. A61B 17/39
[52] U.S. Cl. ........................ 606/45; 606/46; 606/41
[58] Field of Search .......................... 606/41, 42, 45–50; 128/642

[56] References Cited

U.S. PATENT DOCUMENTS

| | | |
|---|---|---|
| 1,586,645 | 6/1926 | Bierman . |
| 3,901,242 | 8/1975 | Storz . |
| 4,033,351 | 7/1977 | Hetzel . |
| 4,202,337 | 5/1980 | Hren et al. ............................ 606/48 |
| 4,637,392 | 1/1987 | Sorochenko . |
| 4,674,498 | 6/1987 | Stasz . |
| 4,765,331 | 8/1988 | Petruzzi et al. . |
| 4,823,791 | 4/1989 | D'Amelio et al. . |
| 4,966,597 | 10/1990 | Cosman . |
| 5,013,312 | 5/1991 | Parins et al. . |
| 5,261,905 | 11/1993 | Doresey, III .......................... 606/45 |
| 5,318,564 | 6/1994 | Eggers .................................. 606/47 |
| 5,336,222 | 8/1994 | Durgin, Jr. et al. . |
| 5,354,296 | 10/1994 | Turkel ................................... 606/41 |
| 5,549,605 | 8/1996 | Hahnen ................................ 606/46 |
| 5,582,610 | 12/1996 | Grossi et al. ......................... 606/46 |
| 5,599,349 | 2/1997 | D'Amelio ............................ 606/46 |

FOREIGN PATENT DOCUMENTS 2419131  4/1974  Germany ............................ 606/46

OTHER PUBLICATIONS

Circon/ACMI Resectoscope Brochure, VaporTome The resection electrode.

Circon/ACMI Resectoscope brochure, VaporTome™ THE Resection Electrode (1 page).

ProSurg Inc. Resectoscope brochure, RollerLoop™ Tissue Effect (1 page).

GYNUS Inc. Resectoscope brochure, RollerLoop™ Tissue Effect (1 page).

ProSurg Inc. Resectoscope brochure, SingleBAR™ Tissue Effect (1 page).

*Primary Examiner*—Michael Peffley
*Attorney, Agent, or Firm*—Fish & Richardson P.C.

[57] ABSTRACT

A surgical instrument electrode having a tissue cutting edge disposed along a front portion and a gap having a depth extending along an axis passing through the front portion and a rear portion wherein the depth terminates in a region between the front portion and the rear portion. With such an arrangement, relatively deep gaps may be formed in the electrode without requiring a corresponding increase in the bluntness of the tissue cutting edge. In addition, the electrode has a cross-sectional shape substantially continuously changing along a portion of the electrode from a substantially circular cross-section at a distal end to a substantially rectangular cross-section along the tissue cutting edge. Due to the continuous nature of the change, undesirable electrical arcing due to the shape change is substantially reduced, and is in effect removed.

18 Claims, 12 Drawing Sheets

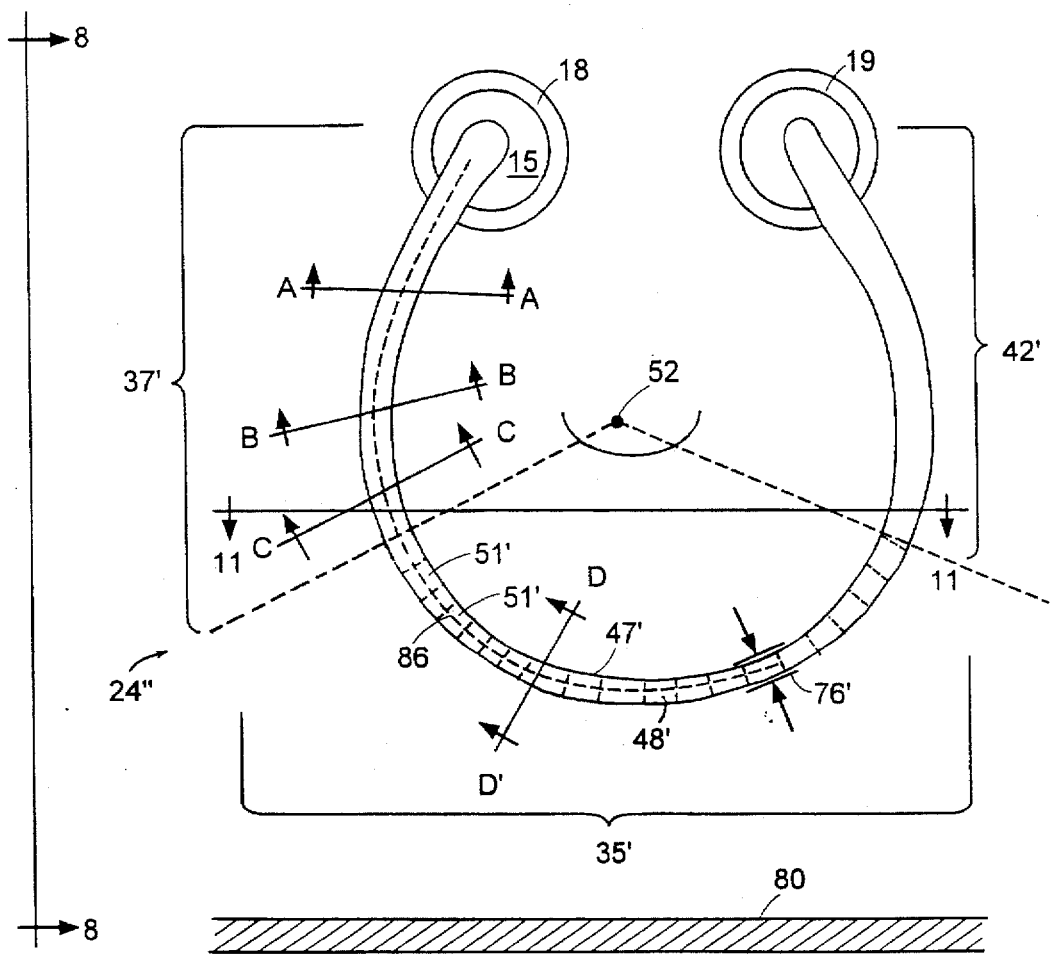
FIG. 7
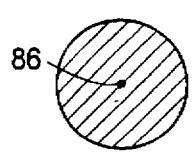  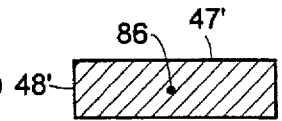 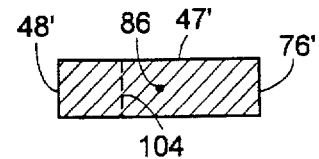
FIG. 7A  FIG. 7B  FIG. 7C  FIG. 7D

ELECTRODE FOR COAGULATION AND RESECTION

BACKGROUND OF THE INVENTION

The invention relates generally to surgical instruments and more particularly to surgical instruments adapted to simultaneously resect and fulgurate animal tissue.

As is known in the art, endoscopic resection of animal tissue is commonly used for resection of animal organs, such as transurethral resection of the bladder or prostate and endometrial ablation. A resectoscope is used for viewing the interior of the organ undergoing resection. The resectoscope typically includes a telescope, an outer sheath housing the telescope, and a handle assembly. A surgical instrument is slid through the telescope to the interior of the organ. The handle assembly is used to move the surgical instrument back and forth with respect to the tissue.

The actual resection of tissue involves using the surgical instrument in a cutting mode. One such surgical instrument carries an electrode. During the cutting mode, a continuous radio frequency (RF) signal is applied to the electrode as the electrode is passed through a slice of the tissue being resected. With a monopolar electrode, the RF signal causes current to pass from the electrode through the tissue and ultimately to a return path through the patient's body. More particularly, in the cutting mode, a surgeon applies to the electrode an RF signal that permits a smooth, easy resection of the slice of tissue that can be evacuated from the organ at the end of the cutting procedure. One limitation of resection by this cutting mode is that bleeding results as the tissue is resected. More particularly, due to the characteristics of the RF signal used in the cutting mode, while tissue is typically desiccated, the RF signal does not adequately stop bleeding. Consequently, after completing the resection with the cutting mode, the surgeon is usually required to return to the tissue's bleeding points and use a coagulation mode to fulgurate thoroughly the bleeding points and thereby stop the resulting bleeding. The coagulation mode uses a different, pulsing RF signal; more particularly, high-intensity RF pulses are fed to the electrode. At the electrode, the high-voltage pulses produce arcing that burns or fulgurates adjacent tissue, thereby stopping the bleeding. The electrode described above is a monopolar electrode, because the current returns via the return path. With bipolar electrosurgical devices, the effect of the current is confined to a small area between two electrodes.

As is also known in the art, monopolar and bipolar electrodes adapted for use in resectoscopes and endoscopes are available with many different shapes, sizes, and functions. The electrodes include blades, needles, balls, loops, spear tips, flexible wires, semicircular wires, spatulas, and blunt tips. U.S. Pat. No. 3,901,242 to Stortz describes an electrosurgical loop device wherein two helically wound, closely spaced electrodes are used with a high frequency bipolar current. U.S. Pat. No. 4,637,392 to Sorochenko describes helically affixed electrodes disposed on an ellipsoid-shaped body to provide bipolar coagulation for hard-to-access places in the human body. U.S. Pat. No. 5,354,296 to Turkel describes a variable morphology bipolar electrode that provides improved coagulation for endometrial ablation over large areas. Compared to monopolar probes, probes using bipolar technologies, such as the aforementioned devices, are typically inadequate and inefficient for resecting and coagulating tissue, especially prostate, bladder and endometrial tissue. Therefore, monopolar electrodes are most commonly used for resecting such tissue. Monopolar electrosurgical devices may, however, injure tissue not intended to be treated and may even cause damage to the surgical target area.

More recently, one surgical instrument has been proposed for simultaneous tissue resection and coagulation. The surgical instrument includes a loop-like electrode having a substantially rectangular cross-sectional shape. The electrode has a cutting surface adapted to be drawn by the surgeon through the tissue as the RF signal is applied to it. Along the electrode loop's outside and substantially perpendicular to the cutting surface is a bottom surface having gaps formed therein and adapted to produce electrical arcing in response to an electrical signal. Thus, arcing is produced at the gaps for simultaneous coagulation of the resected tissue. In general, deeper gaps provide more intense arcing than shallower gaps. However, with the proposed surgical electrode, the deeper the gaps, the broader the cutting surface. As the breadth of the cutting surface is increased to improve coagulation, the cutting edge becomes blunter, thereby reducing resection effectiveness.

SUMMARY OF THE INVENTION

In accordance with one feature of the invention, a surgical instrument is provided with an electrode having a tissue cutting edge disposed along a front portion and a gap having a depth extending along an axis passing through the front portion and a rear portion of the electrode, wherein the depth terminates in a region between the front and rear portions.

With such an arrangement, relatively deep gaps may be formed in the electrode without requiring a corresponding increase in the bluntness of the tissue cutting edge. That is, because the gap's depth extends and terminates as described above, the thickness of the cutting edge of the electrode need not be increased in order to increase the depth of the gap.

In accordance with another feature of the invention, a surgical instrument is provided with an electrode having a tissue cutting edge for resecting tissue. The electrode has a cross-sectional shape substantially continuously changing along a portion of the electrode from a substantially circular cross-section at a distal end to a substantially rectangular cross-section along the tissue cutting edge.

With such an arrangement, it has been found that by configuring the electrode with a continuously changing cross-sectional shape, undesirable electrical arcing due to the shape change is substantially reduced, and is in effect removed. That is, it had been found that with a surgical instrument having a discontinuous change in cross-sectional shape, undesirable arcing is produced across the discontinuity. Here, because the electrode is configured with a continuously changing cross-sectional shape, the undesirable arcing is substantially reduced, and is in effect removed.

In accordance with still another feature of the invention, a surgical instrument is provided with an electrode having a tissue cutting edge disposed along a front portion and a gap having a depth extending along an axis passing through the front portion and a rear portion of the electrode, wherein the depth terminates in a region between the front and rear portions. The electrode has a cross-sectional shape substantially continuously changing along a portion thereof from a substantially circular cross-section at a distal end to a substantially rectangular cross-section along the tissue cutting edge.

With such an arrangement, a surgical instrument is provided to simultaneously resect and fulgurate animal tissue effectively.

Implementations of these aspects of the invention may include one or more of the following features.

The electrode may have multiple gaps, wherein each gap has side walls terminating at a bottom region of the gap and each bottom region is disposed in the rear portion or the front portion.

The electrode may include molybdenum, tungsten, stainless steel or a combination of these. The electrode may be disposed along an arc and the tissue cutting edge may correspond to more than 100 degrees of the arc and to less than 180 degrees of the arc.

The tissue cutting edge may have a thickness of less than 0.04 inch or less than 0.015 inch.

In accordance with yet another feature of the invention, an electrode is provided for a monopolar electrosurgical instrument, which electrode comprises an elongated electrically-conducting member having a distal end, a proximal end, and a longitudinal axis, wherein the proximal end is adapted to be connected to a source of electric current and the distal end terminates in a loop of electrically-conducting metal wire, which loop is disposed at an angle traverse to the longitudinal axis of the member and has a retrograde operating edge defined by a portion of the loop, which portion has a plurality of gaps disposed parallel to the longitudinal axis.

BRIEF DESCRIPTION OF THE DRAWINGS

FIG. 7 is a front view of an electrode according to another embodiment of the invention, such electrode being shown at the distal end of an electrocautery endoscopic resection surgical instrument of FIGS. 1 and 2.

FIGS. 7A–7D show four cross-sectional views of the electrode of FIG. 7, such cross sections being taken along lines A—A through D—D in FIG. 7 at different points along the length thereof of the electrode.

DESCRIPTION OF THE PREFERRED EMBODIMENTS

Figure 1:
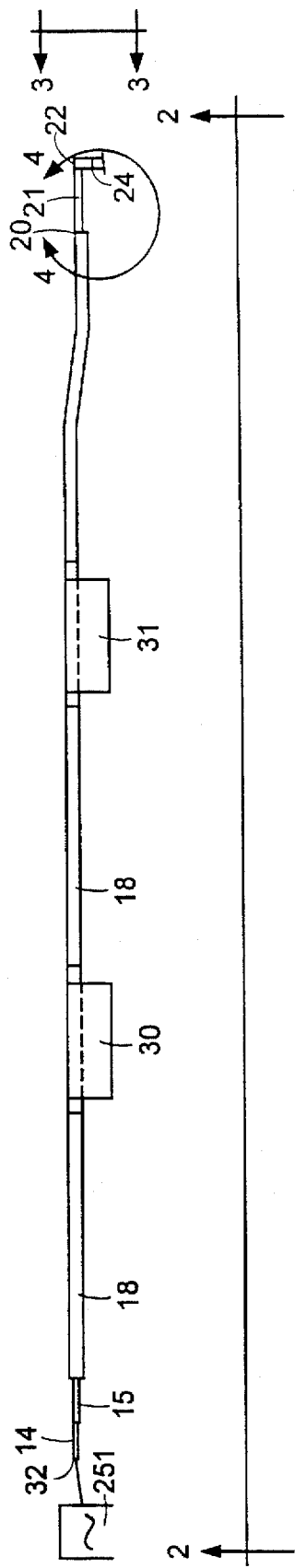
FIG. 1 is a side view of an electrocautery endoscopic resection surgical instrument.
Figure 2:
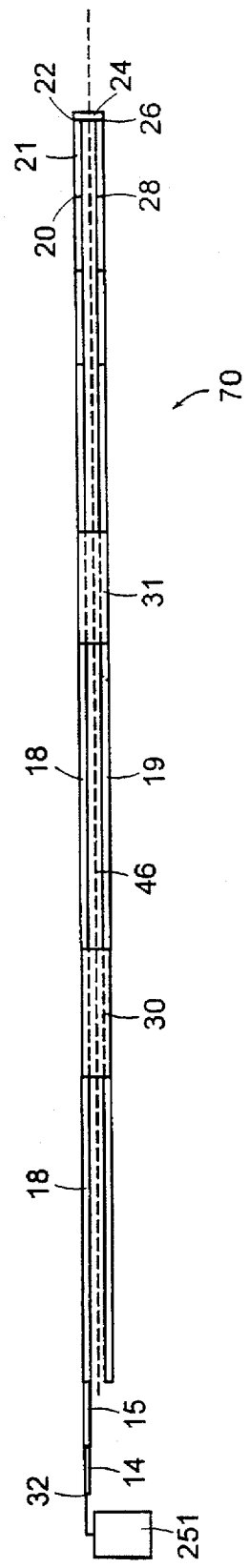
FIG. 2 is a bottom view of the electrocautery endoscopic resection surgical instrument of FIG. 1.

Referring to FIGS. 1–2, a monopolar electrode, described in detail below, is shown disposed at a distal end 22 of an electrocautery resection instrument (elongated electrically-conducting member) 70. The instrument 70 includes an electrically-conducting metal wire 14 surrounded by an insulating material 15. The insulating material 15 is preferably any non-conducting plastic or rubber shrink wrap. In a preferred embodiment, the metal wire 14 is composed of molybdenum, tungsten, or surgical stainless steel, although other electrically conducting metals or materials can be employed. The metal wire 14 has a circular cross-sectional shape and has a diameter between 0.01 inch and 0.04 inch with approximately 0.02 inch being preferred.

Both the metal wire 14 and the insulating material 15 are covered by first and second metal tubings 18, 19. The metal wire 14 and the insulating material 15 extend along the entire length of the first metal tubing 18 and exit the tubing 18 at a distal end 20 of the tubing 18. The metal wire and the insulating material then continue together in an extension 21 having a length of approximately 0.5 inch to 1.0 inch with approximately 0.65 inch being preferred. The metal wire 14 then emerges from the insulating material at the distal end 22 where the metal wire is configured into the electrode 24. The electrode 24 is preferably loop-like, i.e., substantially semi-circular or disposed along an arc, as described in more detail below. The metal wire 14 then reenters the insulating material at another distal point 26, from where the metal wire returns along the length of the instrument. Together, the metal wire and the insulating material reenter the second metal tubing 19 at a distal end 28 of the second tubing 19.

The metal tubings 18, 19 can have nearly any length, but approximately 11 inches is preferred. Although the embodiment in FIGS. 1–2 is shown with two metal tubings 18, 19, one metal tube can also be used. For example, the wire and the insulating material can reenter a single double lumen metal tube or a foreshortened second tube.

At least two metal clips 30, 31 are mounted on the metal tubings 18, 19 to secure the two tubings together and to permit an endoscopic lens to be mounted to the instrument for visualizing the electrode 24. The metal clips 30, 31 can be welded, glued, or compression clipped onto the metal tubings 18, 19 at any points along the tubings. The insulating material 15 runs along the entire length of the wire 14 except at the electrode 24 and at a contact point 32. The contact point (proximal end) 32 is where the wire 14 receives from an electric cautery unit (source of electric current) 251 an electrical signal for passing to the electrode 24. The electrical signal is preferably an RF signal having at least one sinusoidal signal and providing a cutting current. The electrode responds to the signal by generating electrical arcing sufficient for vaporizing tissue.

Figure 3:
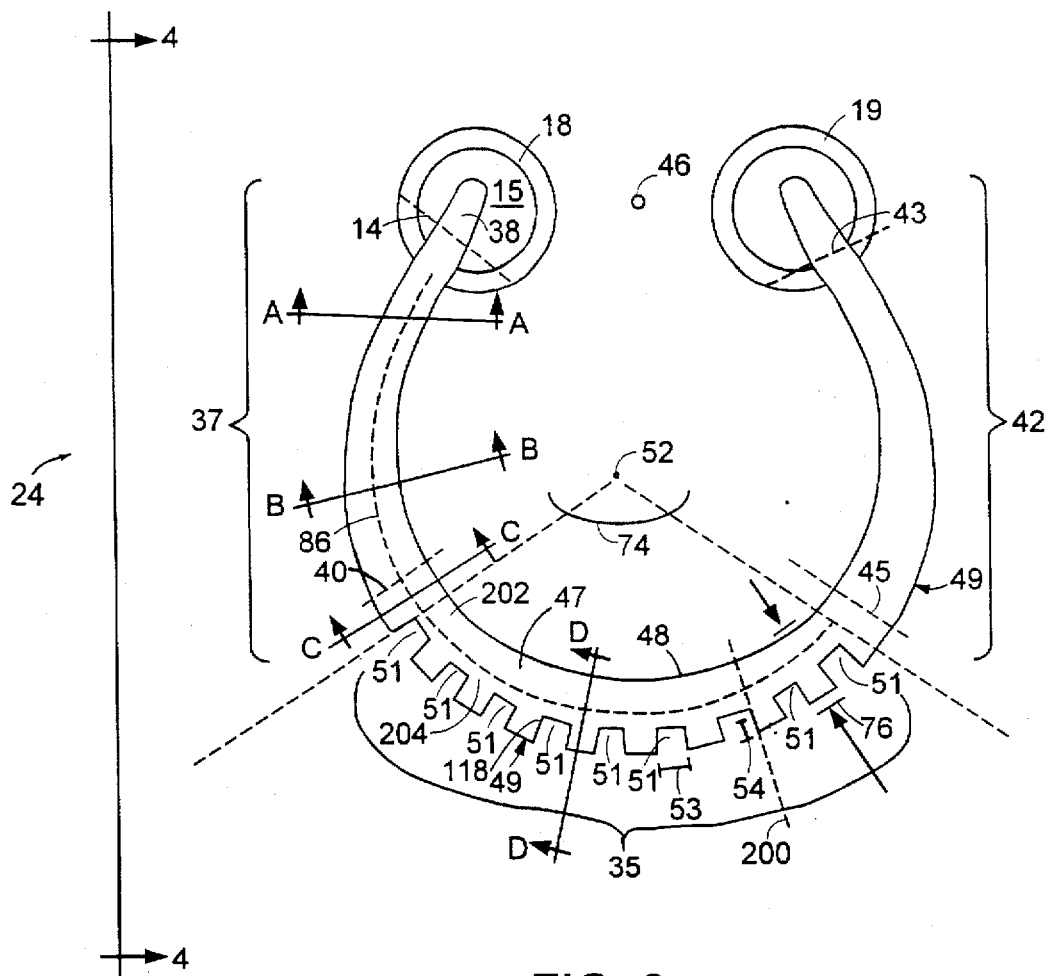
FIG. 3 is a front view of an electrode according to the invention adapted to connection to the distal end of the electrocautery endoscopic resection surgical instrument of FIGS. 1 and 2.
Figures 3A, 3B, 3C, 3D:
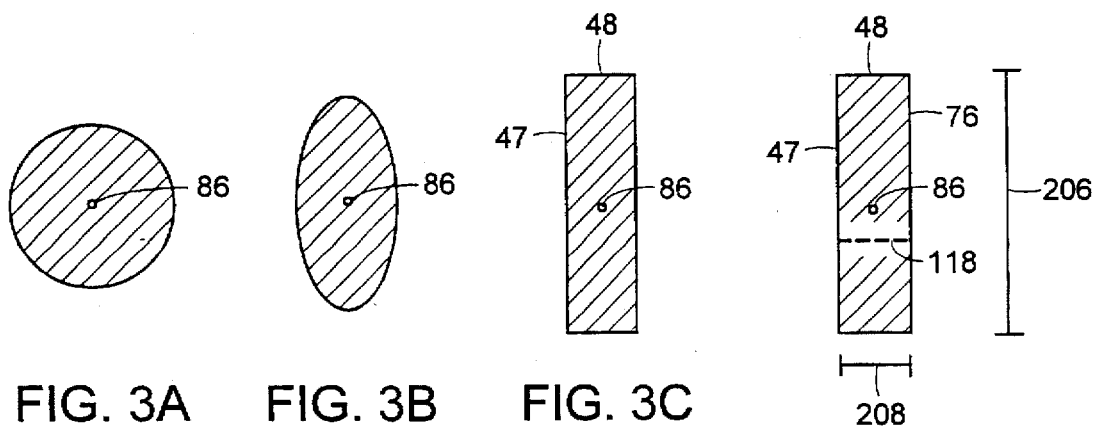
FIGS. 3A–3D show four cross-sectional views of the electrode of FIG. 3, such cross sections being taken along lines A—A through D—D in FIG. 3 at different points along the length thereof of the electrode.
Figure 4:
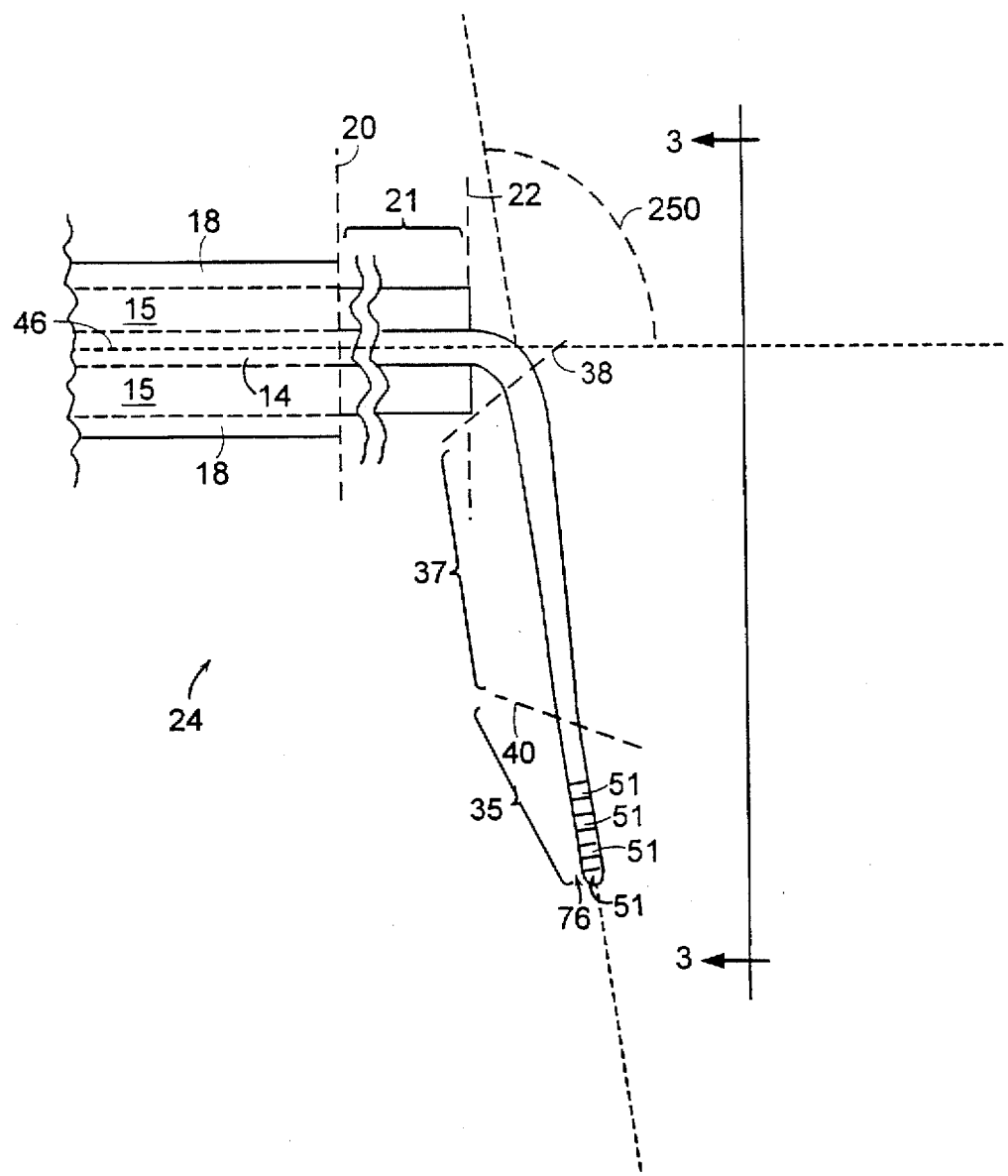
FIG. 4 is a side view of the electrode of FIG. 3.

Referring now to FIGS. 3, 3A–3D, and 4, the electrode 24 is now described in detail. The electrode 24 has a tissue cutting edge (retrograde operating edge) 76 (FIGS. 3, 3D)

for resecting tissue. In addition, the electrode 24 has a cross-sectional shape changing substantially continuously along side regions 37, 42 of the electrode 24. The change is from a substantially circular cross-section at a distal end of the electrode 24, near the insulating material 15, to a substantially rectangular cross-section along the tissue cutting edge 76 of the electrode 24.

The electrode 24 is formed as follows. The metal wire 14 emerges from the distal end 20 of the first metal tubing 18 and from the insulating material 15 at the distal end 22. In a preferred embodiment, the wire 14 then forms a semicircular or arc shape before connecting to the insulating material of the second metal tubing 19. The electrode is disposed at an angle 250 traverse to a longitudinal axis 46 of the instrument.

To take on the electrode 24 loop-like, (i.e., arc or semicircular) shape, the wire 14 curves downward from the distal end 22. As the wire 14 so curves, it gradually flattens from a circular cross-sectional shape to a flattened rectangular cross-sectional shape. The flattened rectangular cross-sectional shape is present in a region 35 having the tissue cutting edge 76. This region 35 of the electrode 24 is rectangular. The side regions 37, 42 of the electrode 24 taper from a mainly circular cross-sectional shape at starting points 38, 43 near the insulating material 15 to a mainly rectangular cross-sectional shape by ending points 40, 45 near the rectangular region 35. Cross-section along line A—A (FIG. 3A), perpendicular to an axis 86 of the wire, demonstrates a circular cross-sectional shape of the wire 14 in the approximate region of one of the starting points 38. Cross-section along line B—B (FIG. 3B) similarly shows an elliptical tapering effect in a mid-portion region 37 as the wire 14 cross-sectional shape changes from circular to flattened rectangular. Likewise, cross-section C—C (FIG. 3C) shows the flattened rectangular configuration achieved by one of the ending points 40. Lastly, cross-section along line D—D (FIG. 3D) demonstrates the same flattened rectangular configuration along the electrode 24 in the rectangular region 35. The dimensions of cross-section along line D—D of the rectangular region 35 are preferably 0.03 inch (FIG. 3D, dimension 206 corresponding to a broad surface 47) by 0.01 inch (FIG. 3D, dimension 208 corresponding to a smaller, narrower surface 48).

The wire 14 can be tapered from a circular to a rectangular configuration by several methods with the preferred methods being by hand or machine pressing, or by metal casting into a mold. In the embodiment shown in FIGS. 3–4, the broad surface 47 is disposed opposite the tissue cutting edge 76 of the rectangular region 35. The broad surface 47 is traverse, here substantially perpendicular, to the length of the instrument, i.e., to the longitudinal axis 46. The small surface 48 is parallel to the same.

FIG. 3 shows the electrode 24 in relation to a center point 52. The rectangular region 35 can vary in size, corresponding to an angle 74 measured from the center point 52. The angle 74 is preferably between 100 degrees and 180 degrees, depending upon the rapidity of the taper of the wire 14 from a circular to a flattened rectangular configuration. In a preferred embodiment, the angle 74 is approximately 120 degrees.

By configuring the electrode 24 with a continuously changing cross-sectional shape, undesirable electrical arcing across the electrode 24 is substantially reduced, and is in effect removed. That is, it had been found that with a surgical instrument having a discontinuous change in cross-sectional shape, undesirable arcing is produced across the discontinuity. The undesirable arcing can cause damage to tissue not intended to be affected by the instrument. In addition, the discontinuity can cause rectification of the electrical signal, resulting in undesirable muscle twitching. Here, however, because the electrode 24 is configured with a continuously changing cross-sectional shape, arcing across the electrode 24 is substantially reduced, and is in effect removed.

The electrode 24 also has multiple gaps 51 formed within an outer portion 49 of the rectangular region 35. Each gap or tooth-like indentation 51 has a depth 54 extending along an axis (e.g., axis 200) that passes through a top portion 202 of the electrode 24 (i.e., through a portion above the axis 86 as shown in FIG. 3) and through a bottom portion 204 of the electrode 24 (i.e., through a portion below the axis 86 as shown in FIG. 3). The depth 54 terminates in a region 118 between the top portion 202 and the bottom portion 204.

In response to the electrical signal providing the cutting current, these gaps 51 provide electrical arcing. Hence, effective coagulation of tissue is provided by the arcing while the instrument is used in the cutting electrocautery mode. The gaps 51 may be curved, square, rectangular, semicircular, or triangular. The gaps 51 may be notches, sawtooth indentations, tooth-like indentations, castellations, grooves, slots, troughs, trenches, and the like, for example. The shapes of the gaps 51 may be symmetrical or asymmetrical. The gaps 51 may be larger in width than in depth or vice versa and may be either uniform or nonuniform in shape and size. The number of gaps 51 along the rectangular region 35 is preferably greater than 5 and less than 20. In FIG. 3, a preferred embodiment is shown with 9 rectangular-shaped gaps 51 measuring 0.015 inch in width 53 and 0.015 inch in depth 54.

In this embodiment, as is apparent from FIG. 3, in order to increase the depth 54 of the gaps 51, the tissue cutting edge 76 must also be made larger and blunter. Increasing the depth of the gaps 51 increases the intensity of the arcing, but increasing the bluntness of the edge 76 reduces the effectiveness of the electrode 24 for resection.

Figure 5:
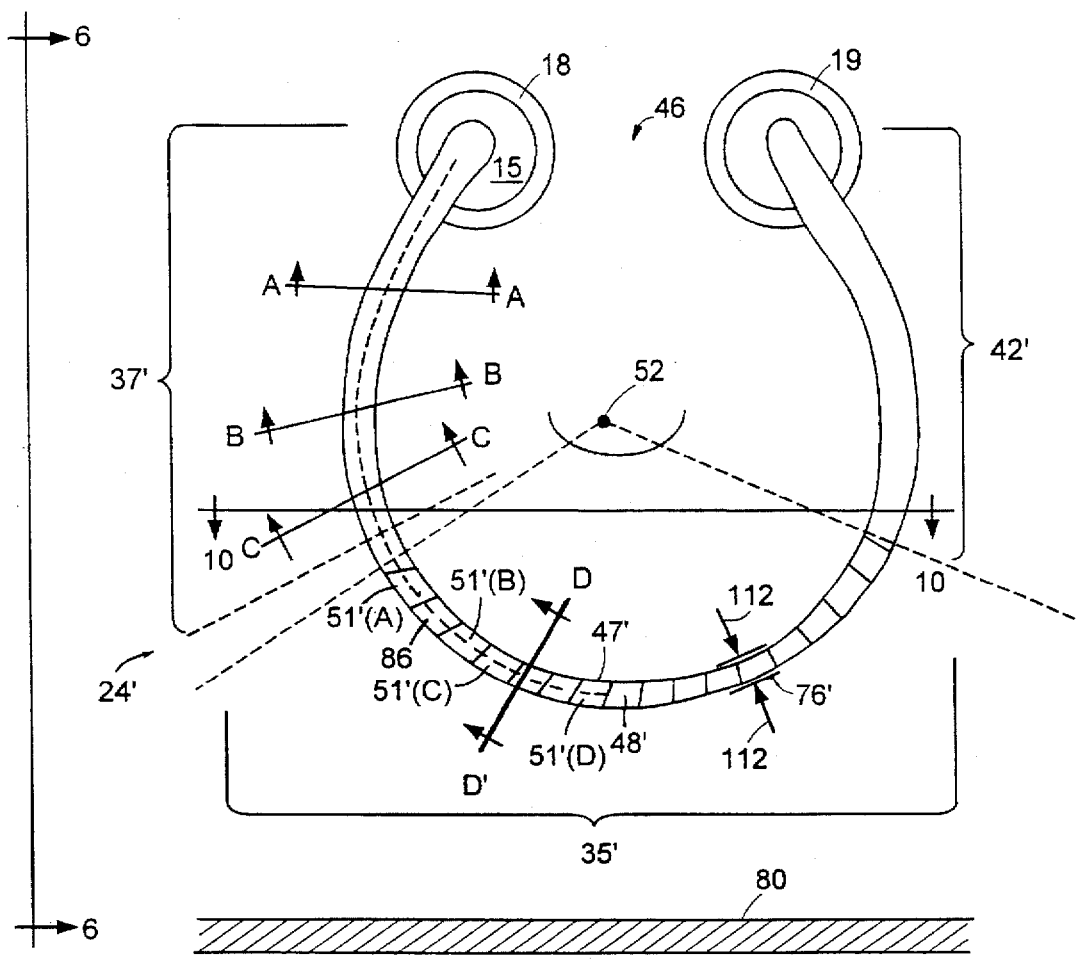
FIG. 5 is a front view of an electrode according to another embodiment of the invention, such electrode being shown at the distal end of an electrocautery endoscopic resection surgical instrument of FIGS. 1 and 2.
Figure 5A:
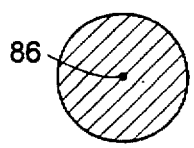
FIGS. 5A–5D show four cross-sectional views of the electrode of FIG. 5, such cross sections being taken along lines A—A through D—D in FIG. 5 at different points along the length thereof of the electrode.
Figure 5B:
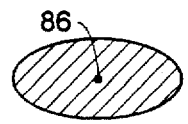
Figure 5C:
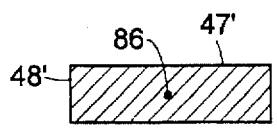
Figure 5D:
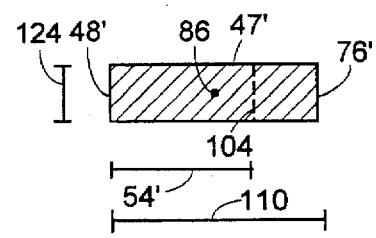
Figure 6:
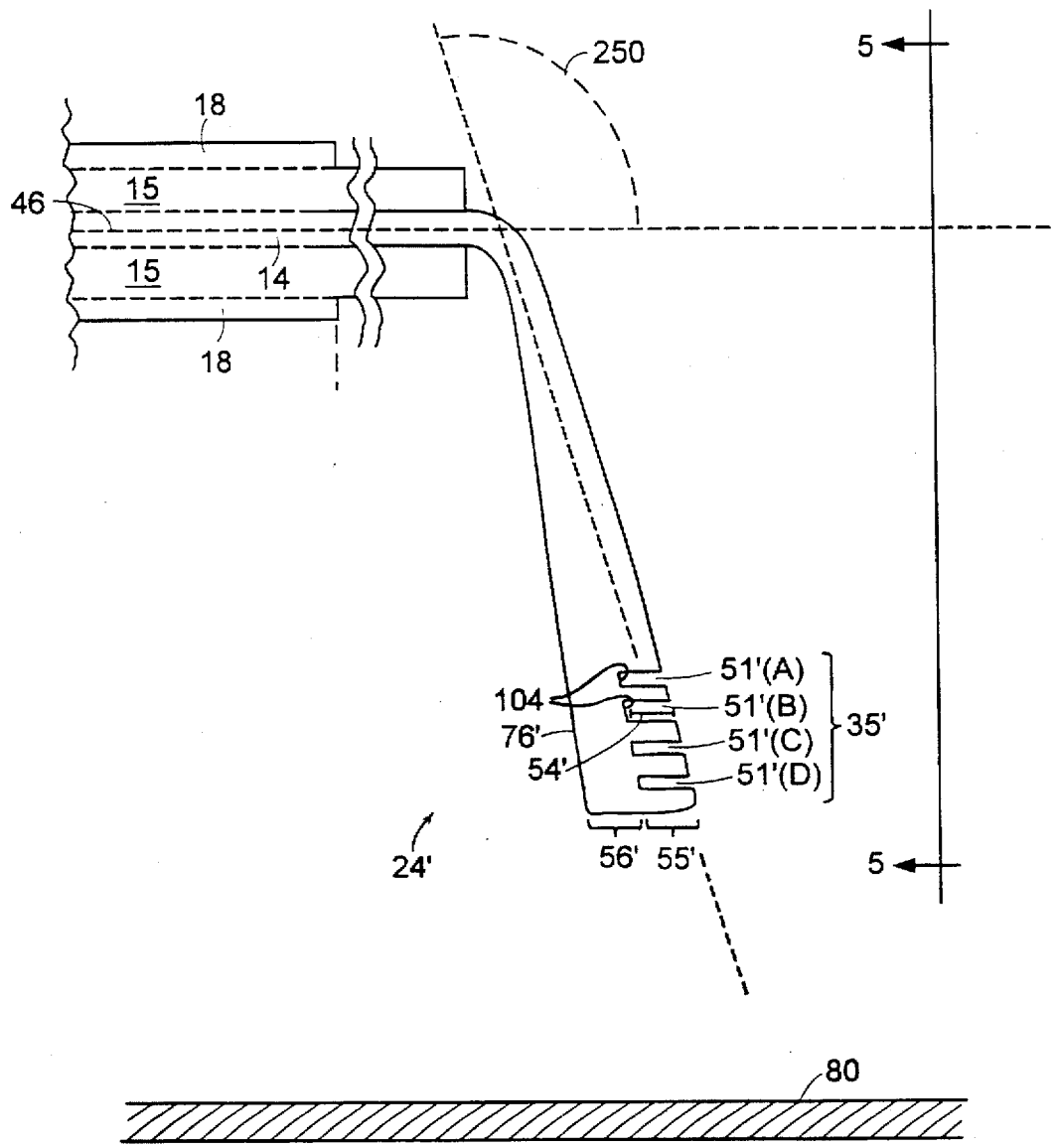
FIG. 6 is a side view of the electrode of FIG. 5.
Figure 8:
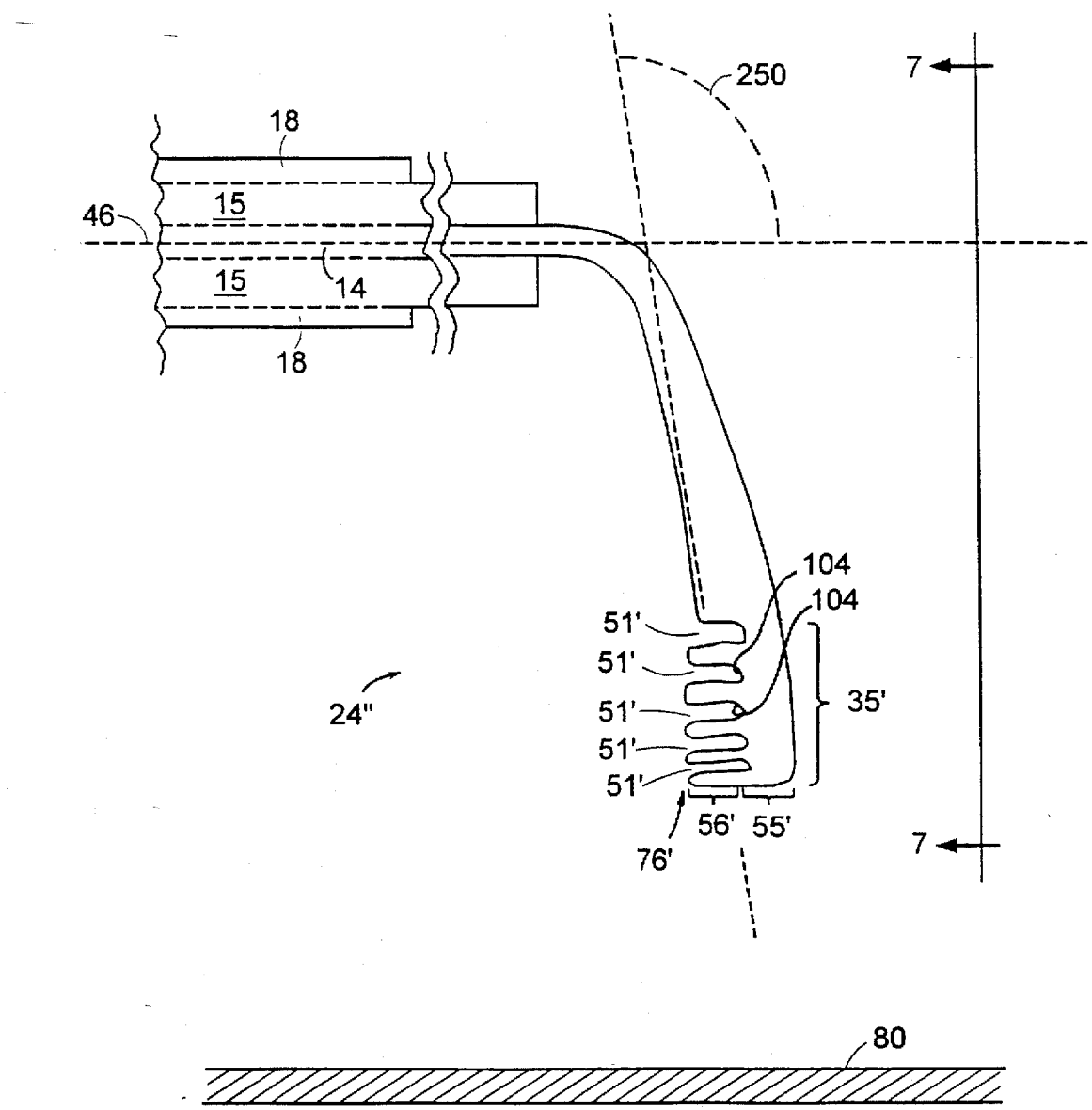
FIG. 8 is a side view of the electrode of FIG. 7.

FIGS. 5, 5A–5D, 6, 9, 10, 11A, and 11B show another electrode 24'. In side regions 37' and 42', the wire 14 used to form electrode 24' is again tapered from a circular cross-sectional shape to a rectangular cross-sectional shape. Cross-sections taken along lines A—A through D—D, respectively, in FIG. 5 are shown in FIGS. 5A–5D, respectively and demonstrate the tapering of one of the side regions 37' from a circular cross-sectional shape to a rectangular cross-sectional shape. However, in electrode 24', a tissue cutting edge 76' is disposed along a front portion 56' of the electrode 24' and multiple gaps 51' are disposed in a rear portion 55' of the electrode 24'. The rectangular region 35' is oriented differently from the orientation of the rectangular region 35 of electrode 24, FIG. 3. Thus, here, electrode 24' has a broad surface 47' corresponding to the rectangular region 35' is substantially parallel to the longitudinal axis 46 of the instrument. A small surface 48' is substantially perpendicular to the longitudinal axis 46. As a result, the small surface 48' is also substantially perpendicular to the broad surface 47'. More particularly, in this embodiment, unlike in the electrode 24 (FIG. 3), the edge 76' is disposed opposite the narrow surface 48', not the broad surface 47'. The gaps 51' are visible along the broad surface 47'.

Figure 10:
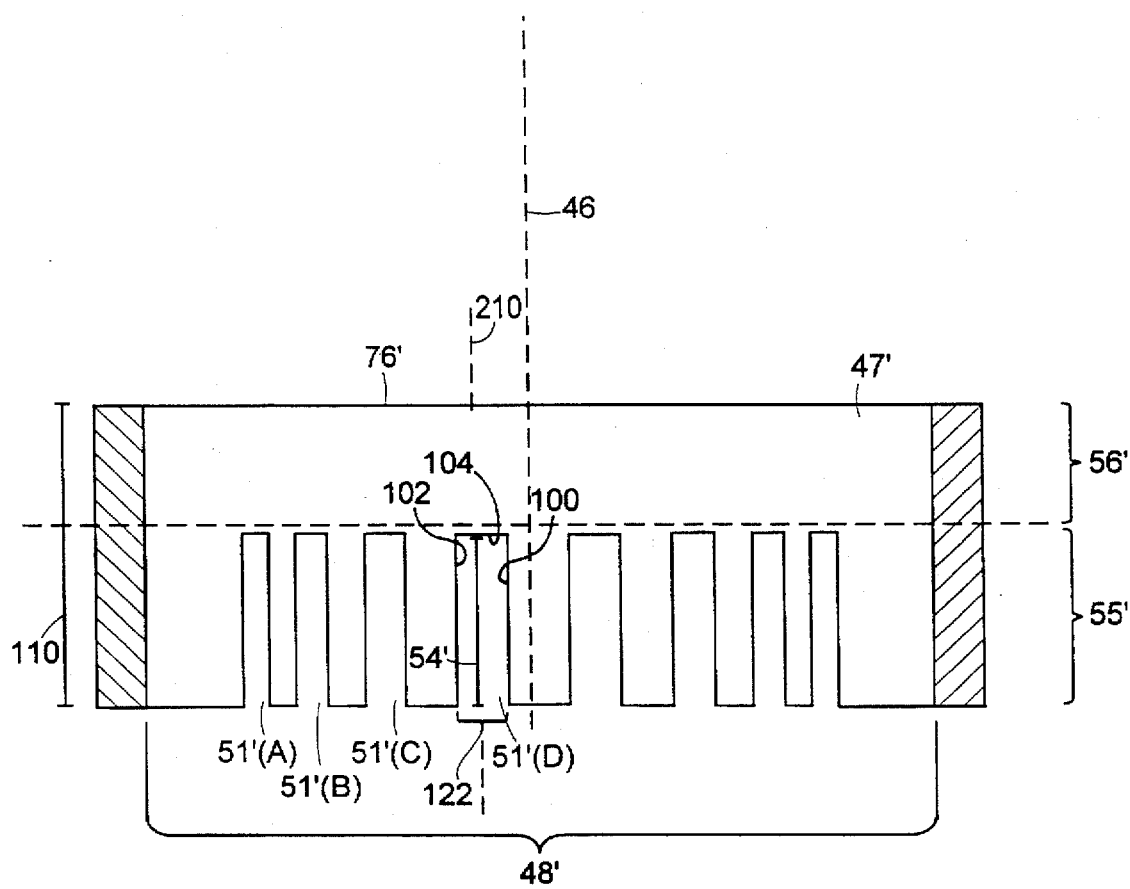
FIG. 10 is a plan cross-sectional view of the electrically conductive electrode of FIGS. 5–6, such cross section being taken along line 10—10 of FIG. 5.
Figure 11A:
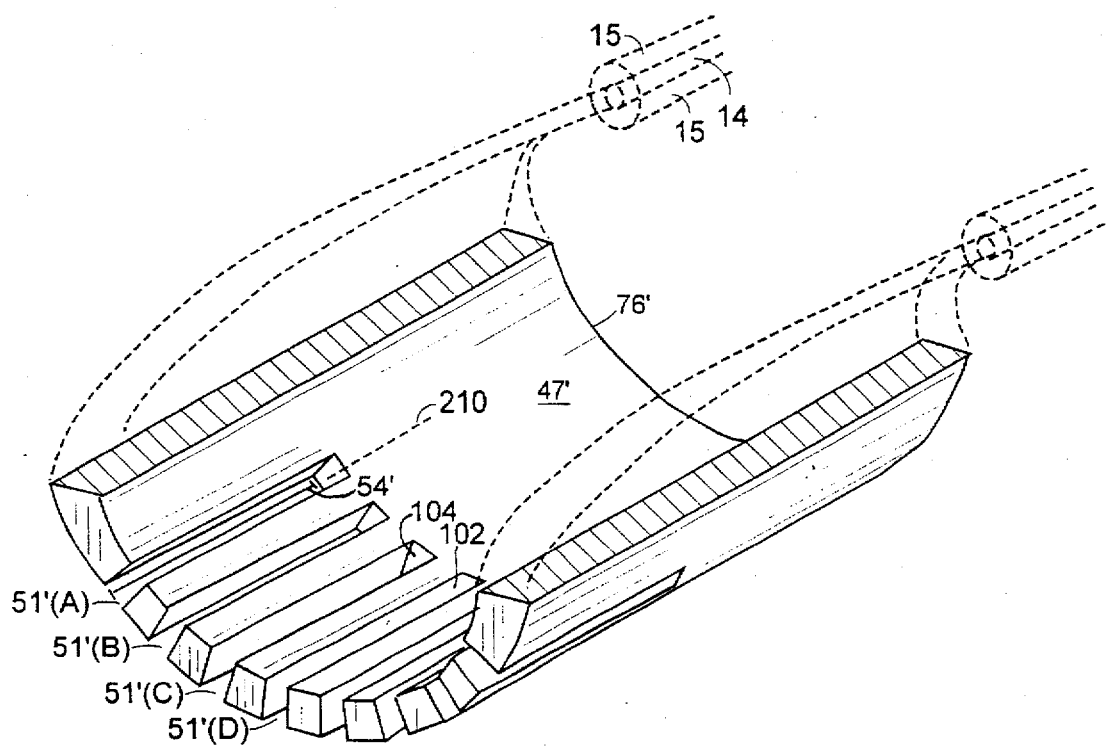
FIG. 11A is a rear isometric cross-sectional view of the portion of the electrode corresponding to FIG. 10, such cross-section being taken along line 10—10 of FIG. 5.
Figure 11B:
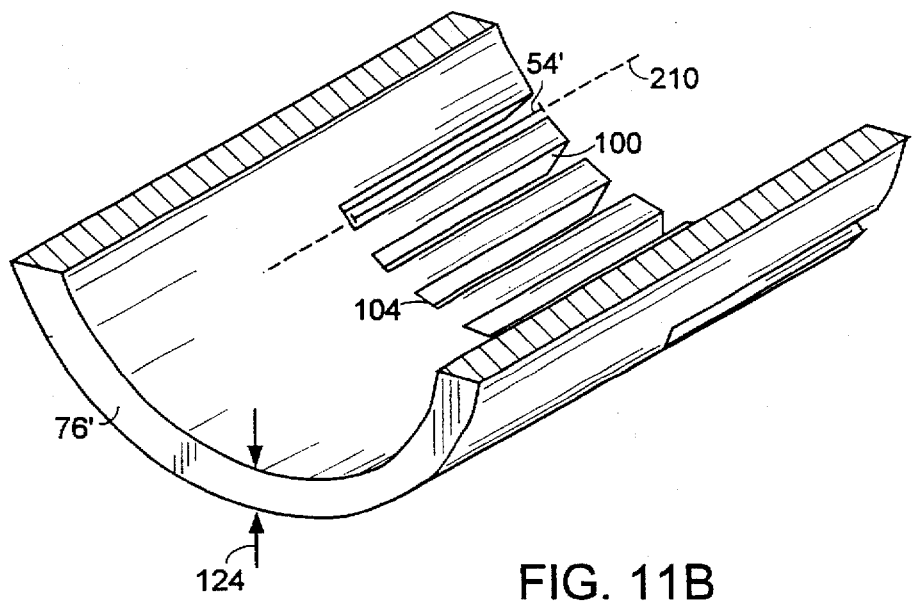
FIG. 11B is a front isometric cross-sectional view of the portion of the electrode corresponding to FIG. 10, such cross-section being taken along line 10—10 of FIG. 5.
Figure 12:
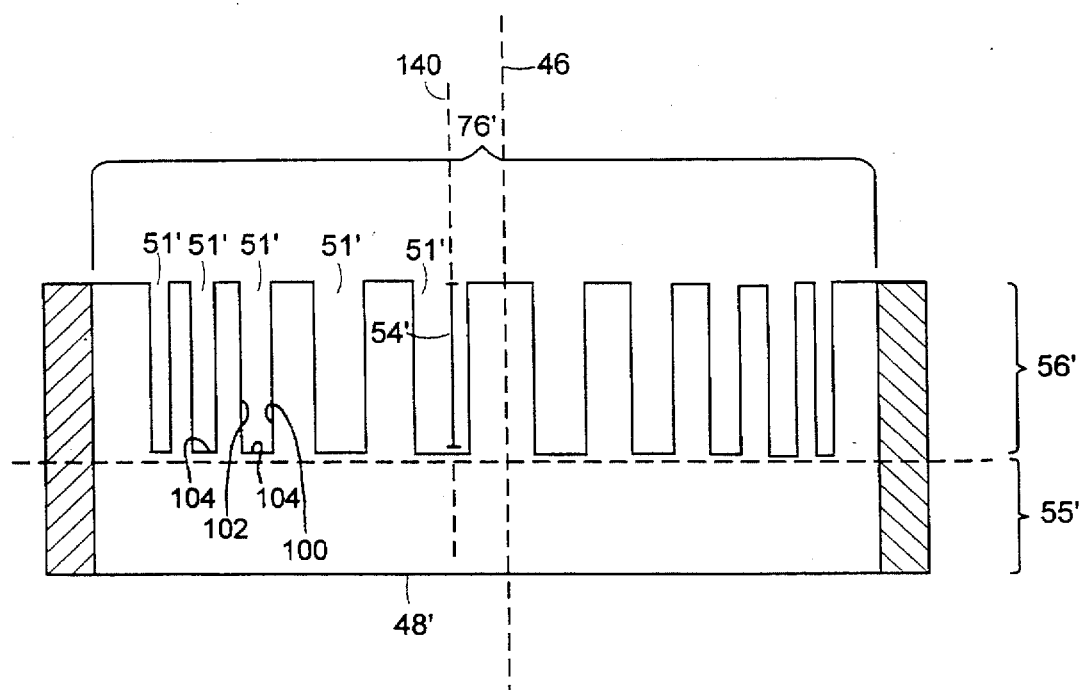
FIG. 12 is a plan cross-sectional view of the electrically conductive electrode of FIGS. 7–8, such cross section being taken along line 11—11 of FIG. 7.
Figure 13:
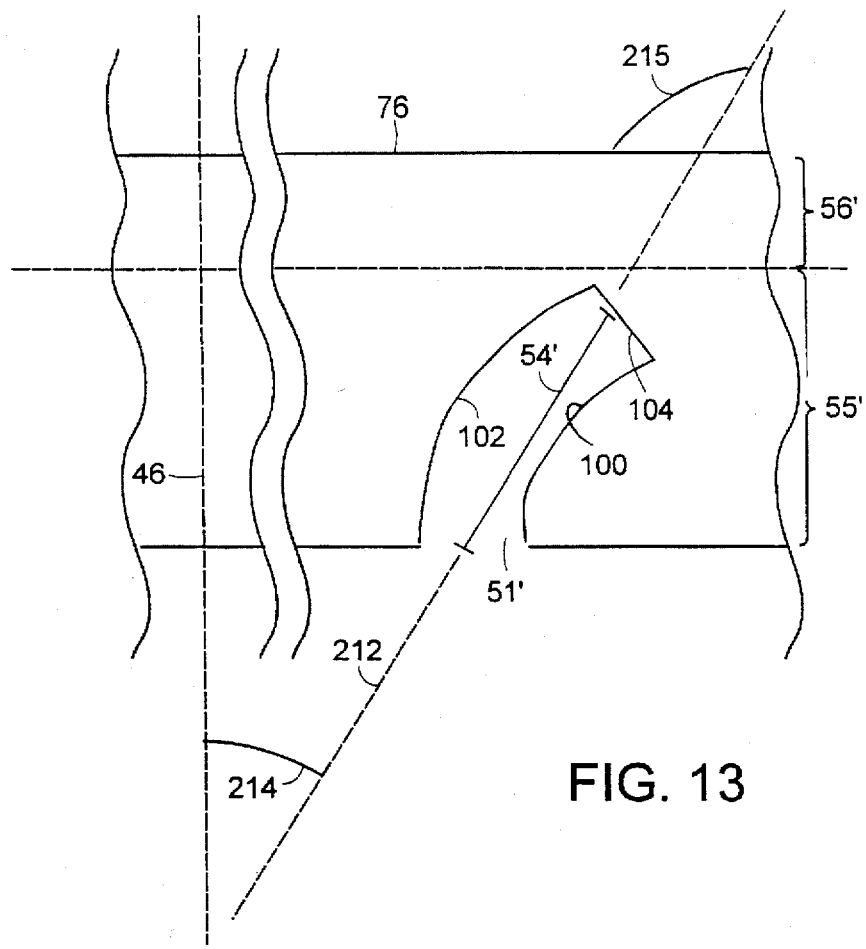
FIG. 13 is a view of an alternative embodiment of a gap.

FIGS. 10, 11A, and 11B show that the tissue cutting edge 76', disposed opposite the narrow surface 48', is disposed along the front portion 56' of the electrode 24' and multiple gaps 51' are disposed in the rear portion 55' of the electrode 24'. Each gap 51' has side walls 100, 102 terminating at a bottom region 104 of the gap 51'. The bottom region 104 is disposed in the rear portion 55' of the electrode 24'. An open region 122 of each gap 51' is at the rearmost end of the rear portion 55'. Each gap 51' also has a depth 54' extending along an axis 210 passing through the front portion 56' and the rear portion 55'. The axis 210 is not necessarily parallel to the longitudinal axis 46 and is not necessarily perpendicular to the tissue cutting edge 76'. (In fact, as shown in FIG. 13, the axis 212 along which the depth extends may instead be at an oblique angle 214 or 215 to the longitudinal axis 46 or the tissue cutting edge 76' or both.)

Figure 9:
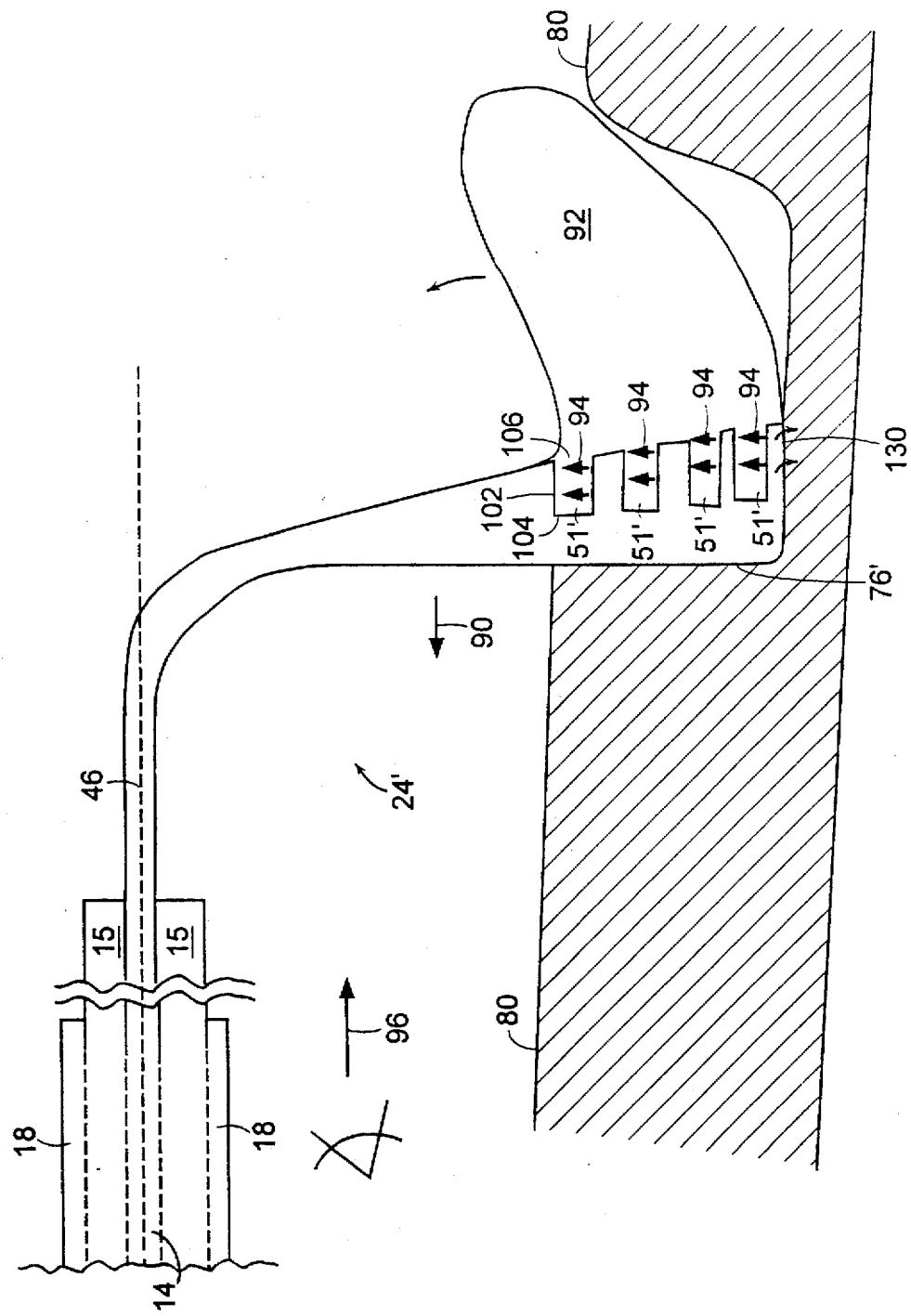
FIG. 9 is a side view of the electrically conductive electrode of FIGS. 5–6, the being shown resecting tissue.

With such an arrangement (FIG. 10), unlike electrode 24 (FIG. 3) having gaps 51, with electrode 24' relatively deep gaps 51' may be formed in the electrode 24' without requiring a corresponding increase in a thickness 124 (FIGS. 5D and 11B), (i.e., bluntness) of the tissue cutting edge 76'. In this particular embodiment, the thickness 124 is the same dimension as the width of the narrow surface 48'. As shown in FIG. 9, the corresponding increase in thickness is avoided because the gaps are disposed away from a resection direction 90, thus providing no effective drag on or impediment to resection. The gaps 51' are disposed behind the cutting edge 76' and are preferably substantially obscured by the edge 76' when the electrode 24' is viewed from a viewing direction 96 opposite the resection direction 90 and parallel to the longitudinal axis 46. Thus, the depth 54' of the gaps 51' is made substantially independent of the bluntness of the tissue cutting edge 76', allowing gaps 51' to be made deep enough for effective fulguration without requiring a trade-off in resection effectiveness. For example, the depth 54' of one or more of the gaps 51' may be such that the gap 51' extends at least halfway into the electrode 24'. That is, the depth 54' may be at least half an electrode 24' thickness 110 (FIG. 5D) corresponding to the broad surface 47'.

In a preferred embodiment, the thickness 124 of electrode 24', also pointed out by the arrows 112 associated with the edge 76' in FIG. 5, is approximately 0.01 to 0.015 inch. That is, when the electrode 24' is viewed along the longitudinal axis 46, the electrode 24' presents a profile, in the rectangular region 35 of the tissue cutting edge 76', of about 0.01 to 0.015 inch in thickness. The edge 76' is preferably no thicker than 0.04 inch, because resection effectiveness is reduced otherwise. In addition, the edge 76' is preferably at least 0.005 inch in thickness, in order to retain effective strength in the electrode 24'.

As the electrode 24' is drawn in the direction 90 of resection (i.e., is moved in a retrograde fashion toward the operator of the instrument) (FIG. 9), the edge 76' is able to cause resection of the tissue 80 to produce a piece 92. Simultaneously, in response to the electrical signal described above with respect to the gaps 51, the gaps 51' provide electrical arcing, either between the side walls 100, 102 of each gap 51', as shown by arrows 94, or from the electrode 24' to the resected tissue 80 shown by another arrow 130, or both. The side walls 100, 102 and the regions 104, 106 of each gap 51' are preferably arranged to provide the gap 51' with a substantially rectangular shape. In other respects, the gaps 51' have characteristics similar to the characteristics of the gaps 51 described above for electrode 24 in connection with FIG. 3. The gaps 51' may be curved, square, rectangular, semicircular, or triangular. The gaps 51' may be notches, sawtooth indentations, tooth-like indentations, castellations, grooves, slots, troughs, trenches, and the like, for example. The shapes of the gaps 51' may be symmetrical or asymmetrical. The gaps 51' may be larger in width than in depth or vice versa and may be either uniform or nonuniform in shape and size. The number of gaps 51' along the rectangular region 35 is preferably greater than 5 and less than 20. Bleeding resulting from the resection of the tissue 80 is substantially and simultaneously stopped by the arcing, substantially eliminating a need for the surgeon to return to the resected tissue to fulgurate the tissue.

Alternatively, the electrode 24' may be drawn along the top of the resected tissue surface 80, completely vaporizing tissue 80 in layers to avoid producing a resected piece. Drawing the electrode 24' along the top may be preferred when producing a piece is unnecessary, when subsequent evacuation of the piece is impossible or impractical, or when the tissue 80 to be resected is small enough to be resected effectively by vaporizing layers.

FIGS. 7, 7A-7D, 8, and 12 show electrode 24". In this embodiment, the regions 37' and 42' of electrode 24" are tapered as in the previous embodiment and the gaps 51'. Once again, the broad surface 47' of the rectangular region 35' is parallel to the longitudinal axis 46 of the instrument. However, with electrode 24", the multiple gaps 51' are disposed in the front portion 56' of the rectangular region 35' (i.e., in the cutting edge 76'). The depth 54' of each gap 51' extends along an axis 140 passing through the front portion 56' and the rear portion 55'. The axis 140 is not necessarily parallel to the longitudinal axis 46 and is not necessarily perpendicular to the tissue cutting edge 76'. In fact, as discussed above with respect to the previously described electrode 24', the axis 140 may instead be at an oblique angle to the longitudinal axis 46 or the tissue cutting edge 76' or both. In other respects, the gaps 51' of electrode 24" are similar to the gaps 51' of the electrode 24" (FIG. 5).

Figure 14:
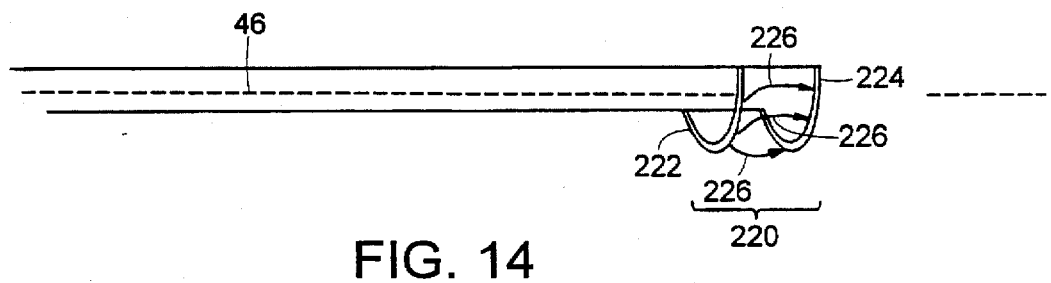
FIG. 14 is a view of a bipolar electrode having two monopolar electrodes.

The electrode 24, 24', or 24" may be used or combined in tandem to thereby provide in such a combination a bipolar electrode 220 as shown in FIG. 14. The bipolar electrode 220 includes a first monopolar electrode 222 and a second monopolar electrode 224. Each monopolar electrode 222 or 224 is electrode 24, 24', or 24". With the bipolar electrode 220, arcing 226 is produced between the first monopolar electrode 222 and the second monopolar electrode 224.

The electrode 24, 24', or 24" is preferably constructed of molybdenum, tungsten, stainless steel or any electrically conducting material. In a preferred embodiment, molybdenum is used, because molybdenum is soft and malleable. The softness and malleability permit mechanical deforming of the electrode 24, 24', 24' to create the gaps 51 or the gaps 51' without fracturing the metal. In a preferred embodiment, the deforming is produced by electrical discharge machining ("EDM").

What is claimed is:

1. An electrode for a monopolar electrosurgical instrument, which electrode comprises an elongated electrically-conducting member having a distal end, a proximal end, and a longitudinal axis, wherein the proximal end is adapted to be connected to a source of electric current and the distal end terminates in a loop of electrically-conducting metal wire, which loop is disposed at an angle of at least 45 degrees transverse to the longitudinal axis of the member and has top and bottom portions, each having a respective outward area defined by a respective substantially uniform surface, and a retrograde operating edge defined by another portion of the loop, which portion has a plurality of gaps disposed parallel to the longitudinal axis.

2. A surgical instrument, comprising:
   a monopolar electrode having:
   a tissue cutting edge disposed along a front portion;
   a cross-sectional shape having a substantially rectangular cross section along said tissue cutting edge, said cross-sectional shape substantially continuously changing along a portion of said electrode from a substantially circular cross-section at a distal end of said electrode to said substantially rectangular cross-section along said tissue cutting edge; and a gap having a depth extending along an axis passing through the front portion and a rear portion of the electrode, the depth terminating in a region between the front portion and the rear portion.

3. A surgical instrument having a longitudinal axis, comprising:

a monopolar electrode disposed at an angle of at least 45 degrees to the longitudinal axis, the electrode having:

top and bottom portions, each having a respective outward area defined by a respective substantially uniform surface;

a front portion and a rear portion;

a tissue cutting edge disposed along the front portion; and a gap having a depth extending along an axis passing through the front portion and the rear portion of the electrode, the depth terminating in a region between the front portion and the rear portion.

4. The surgical instrument of claim 3, wherein said electrode has a cross-sectional shape having a substantially rectangular cross-section along said tissue cutting edge.

5. The surgical instrument of claim 3 wherein the gap extends from the front region.

6. The surgical instrument of claim 3 wherein the gap extends from the rear region.

7. The surgical instrument of claim 5, wherein the gap has side walls terminating at a bottom region of the gap, the bottom region being disposed in the front portion.

8. The surgical instrument of claim 5, wherein
the electrode comprises a plurality of gaps; and
each gap has side walls terminating at a bottom region of the gap, each bottom region being disposed in the front portion of the electrode.

9. The surgical instrument of claim 6, wherein the gap has side walls terminating at a bottom region of the gap, the bottom region being disposed in the rear portion.

10. The surgical instrument of claim 6, wherein
the electrode comprises a plurality of gaps; and
each gap has side walls terminating at a bottom region of the gap, each bottom region being disposed in the rear portion of the electrode.

11. The surgical instrument of claim 3, wherein the electrode comprises molybdenum.

12. The surgical instrument of claim 3, wherein the electrode comprises stainless steel.

13. The surgical instrument of claim 3, wherein the electrode comprises tungsten.

14. The surgical instrument of claim 3, wherein the gap is configured to produce electrical arcing in response to an electrical signal.

15. The surgical instrument of claim 14, wherein the electrical signal comprises a sinusoidal signal.

16. The surgical instrument of claim 3, wherein the tissue cutting edge has a thickness of less than 0.04 inch.

17. The surgical instrument of claim 3, wherein the tissue cutting edge has a thickness of less than 0.015 inch.

18. The surgical instrument of claim 3, wherein
the electrode is disposed along an arc; and
the tissue cutting edge corresponds to more than 100 degrees of the arc and to less than 180 degrees of the arc.

* * * * *